US006241802B1

(12) United States Patent
Spears et al.

(10) Patent No.: US 6,241,802 B1
(45) Date of Patent: *Jun. 5, 2001

(54) METHOD FOR DELIVERY OF GAS-ENRICHED FLUIDS

(75) Inventors: J. Richard Spears, Bloomfield, MI (US); Richard J. Crilly, Windsor (CA)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/500,127

(22) Filed: Feb. 8, 2000

Related U.S. Application Data

(60) Continuation of application No. 09/174,739, filed on Oct. 19, 1998, now abandoned, which is a division of application No. 08/840,908, filed on Apr. 16, 1997, now abandoned, which is a continuation-in-part of application No. 08/453,660, filed on May 30, 1995, now Pat. No. 5,735,934, which is a division of application No. 08/273,652, filed on Jul. 12, 1994, now Pat. No. 5,569,180, which is a continuation-in-part of application No. 08/152,589, filed on Nov. 15, 1993, now Pat. No. 5,407,426.

(51) Int. Cl.[7] .................................................... C21C 5/30
(52) U.S. Cl. .......................... 75/414; 75/559; 48/197 R; 62/66; 134/42; 162/1; 210/758; 435/818
(58) Field of Search .................. 75/414, 559; 48/197 R; 62/66; 134/42; 162/1; 210/758; 435/818

(56) References Cited

U.S. PATENT DOCUMENTS

| | | | |
|---|---|---|---|
| 4,071,443 | 1/1978 | Gorski et al. | 210/7 |
| 4,442,843 | 4/1984 | Rasor et al. | 128/660 |
| 4,657,756 | 4/1987 | Rasor et al. | 424/9 |
| 4,664,680 | 5/1987 | Weber | 55/48 |
| 4,681,119 | 7/1987 | Rasor et al. | 128/660 |
| 4,973,558 | 11/1990 | Wilson et al. | 435/240.242 |
| 5,407,426 | 4/1995 | Spears | 4/24 |
| 5,569,180 | 10/1996 | Spears | 604/24 |
| 5,599,296 | 2/1997 | Spears | 604/26 |
| 5,670,094 | 9/1997 | Sasaki et al. | 261/27 |
| 5,693,017 | 12/1997 | Spears et al. | 604/132 |
| 5,730,935 | * 3/1998 | Spears | 422/44 |
| 5,735,934 | 4/1998 | Spears | 75/414 |

FOREIGN PATENT DOCUMENTS

4105726C1   9/1992   (DE) .
2 320 908   3/1977   (FR) .

* cited by examiner

Primary Examiner—Melvyn Andrews
(74) Attorney, Agent, or Firm—Margaret A. Kivinski

(57) ABSTRACT

A system and method for delivering a gas-supersaturated fluid comprising a fluid reservoir, a fluid pump, a gas source, a high pressure gas exchanger, and one or more arrays of capillary channels is disclosed. Suitable controls such as differential pressure gauge and valves are provided to maintain a near constant hydrostatic pressure of the fluid within the semi-permeable membrane gas-fluid interface of the gas exchanger at approximately 1% to 20% higher than the gas partial pressure of the fluid within the gas exchanger. Gas-supersaturated fluid output from the gas exchanger via the capillary channels is at a flow velocity of greater than 0.05 m/sec, thereby facilitating delivery of large flow rates of gas-supersaturated fluids without cavitation inception.

38 Claims, 2 Drawing Sheets

METHOD FOR DELIVERY OF GAS-ENRICHED FLUIDS

CROSS-REFERENCE TO RELATED APPLICATIONS

This application is a continuation of U.S. patent application Ser. No. 09/174,739, filed Oct. 19, 1998 now abandoned, which is a divisional application of U.S. patent application Ser. No. 08/840,908, filed Apr. 16, 1997, now abandoned, which is a continuation-in-part of copending U.S. patent application Ser. No. 08/453,660, filed May 30, 1995 (now U.S. Pat. No. 5,735,934), which is a divisional application of U.S. patent application Ser. No. 08/273,652, filed Jul. 12, 1994 (now U.S. Pat. No 5,569,180), which is a continuation-in part of U.S. patent application Ser. No. 08/152,589, filed Nov. 15, 1993 (now U.S. Pat. No. 5,407,426), each of which is hereby incorporated by reference.

FIELD OF THE INVENTION

The present invention generally relates to a system and method for delivering gas-supersaturated fluids. More specifically, the present invention relates to a system and method for delivering gas-supersaturated fluids to a gas-depleted site without the premature formation of bubbles.

BACKGROUND OF THE INVENTION

In many industrial and clinical environments, it is desirable to deliver a gas-enriched fluid to a site of interest, and/or increase the gas concentration of a fluid without a significant increase in the fluid volume.

For example, a fire may be extinguished by delivering an inflammable or an inert gas, such as carbon dioxide or nitrogen, rapidly to the fire via a fluid transporting medium. Environmental problems presented by toxic site cleanups may be ameliorated by delivering a high concentration of a neutralizing or cleansing gaseous agent to the toxic site. The oxygenation level of ponds used in fish farms, and the oxygenation level of waste streams (prior to their release into the environment) may also be increased by delivery of oxygen-enriched fluids to the ponds or streams.

One method of obtaining an increase in the gas concentration level without significant increase in fluid volume is by directly pumping a desired gas into a fluid site of interest. However, such direct pumping is not always efficient and may thereby result in an insufficient increase in gas concentration. Where a noxious gas is used, direct pumping also poses waste engineering problems and/or health hazard due to the presence of any unabsorbed noxious gas.

Another method of obtaining an increase in the gas concentration level without significant increase in fluid volume is by infusing a gas-enriched fluid, such as a gas-supersaturated fluid, into the site of interest. To create a gas-supersaturated fluid, high pressure compression of a gas-liquid mixture can be performed, for example, with the use of a high pressure gas exchanger. Prior art systems for producing gas-supersaturated fluids typically require the use of a high pressure vessel to provide dwell time for dissolving gas nuclei in the fluid outputted from the high pressure gas exchanger. Two such prior art systems are U.S. Pat. No. 5,407,426, "Method and Apparatus For Delivering Oxygen Into Blood" to Spears and U.S. Pat. No. 5,569,180, "Method For Delivering A Gas-Supersaturated Fluid To A Gas-Depleted Site And Use Thereof" to Spears.

In addition, gas nuclei may be present in the fluid prior to supersaturating the fluid with gas. For example, gas nuclei may be dust particles suspended in the fluid or crevices in the container wall in which gas is trapped or absorbed. The presence of gas nuclei facilitates cavitation inception (or, bubble formation), resulting in release of gas from the liquid and thereby decreasing the gas concentration of the fluid.

Furthermore, some prior art systems also require a high pressure (>70 bar) fluid pump to deliver the gas-supersaturated fluid. Particularly in industrial applications (where it may be necessary to deliver large volumes of a gas-enriched fluid to a site of interest), such prior art systems may prove impractical because of the overall complexity, cost, and time associated with operating them.

Another problem associated some of the prior art devices in infusing gas-supersaturated fluid from a high pressure vessel into a site of interest is that cavitation inception at or near the exit ports often results. Cavitation inception may occur because ejection of the fluid into an atmospheric environment results in a decrease in the hydrostatic pressure of the fluid below the gas partial pressure. Disturbances at or near the exit ports may further facilitate cavitation inception. When cavitation takes place, gas is released from the fluid, decreasing its gas concentration. Furthermore, the presence of bubbles in the fluid generates turbulence and impedes the flow of the fluid beyond the exit ports.

Accordingly, there remains a need in the art for a simple, efficient and cost-effective system and method for producing and delivering gas-supersaturated fluid to a site of interest which does not require a high pressure vessel to provide dwell time and which does not require a high pressure fluid pump for delivery of the gas-supersaturated fluid. There remains a further need for a system and method for producing and delivering gas-supersaturated fluid to a site of interest without cavitation inception in the fluid during ejection, particularly at or near the exit ports.

SUMMARY OF THE INVENTION

Preferred embodiments of the present invention meet the foregoing needs by providing a system and method for delivering gas-enriched fluid to a site of interest. Such a system includes a fluid reservoir, a fluid pump, a gas source, a high pressure gas exchanger, and one or more arrays of capillary channels for delivery of gas-supersaturated fluid. Differential pressure gauges and other suitable controls may be provided to maintain a near constant hydrostatic pressure of the fluid throughout the delivery system that is approximately 1% to 20% higher than the gas pressure within the housing of the high pressure gas exchanger. The delivery system may also include a fluid filter for filtering the fluid before it enters the fluid reservoir.

The system and method of the present invention requires relatively low hydrostatic pressures and eliminates the need for a high pressure vessel for providing a dwell time for dissolving gas nuclei in the fluid. The system and method of the present invention also eliminates the need for a high pressure fluid pump for high output delivery of the gas-supersaturated fluid. Furthermore, the system and method of the present invention reduces or eliminates gas nuclei on the inner surface of the exit ports through which the gas-supersaturated fluid exits, in part by providing exit ports with a relatively small diameter.

DETAILED DESCRIPTION OF THE INVENTION

Figure 1:
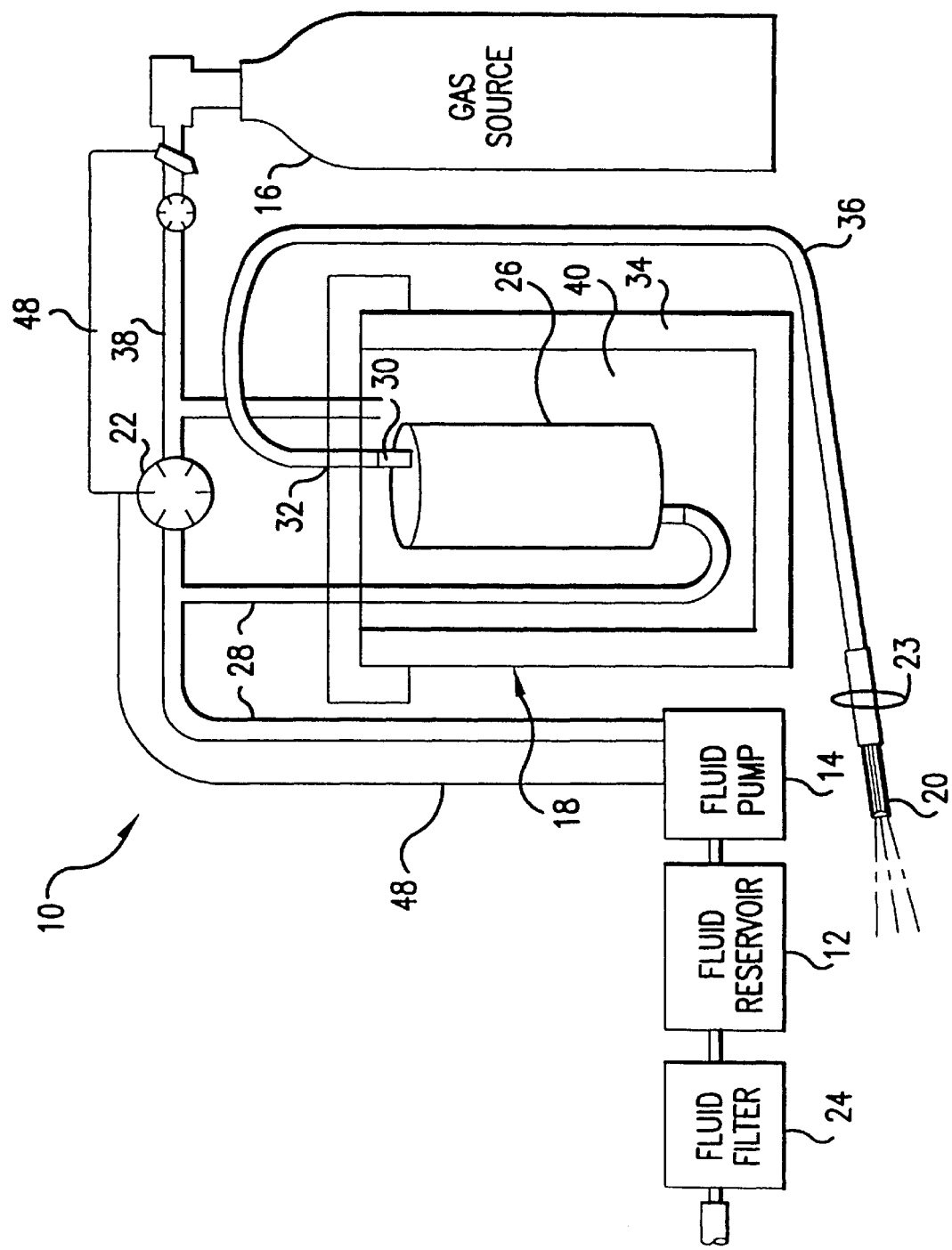
FIG. 1 shows a system for delivery of gas-supersaturated fluids according to a preferred embodiment.

The structure and function of the preferred embodiments can best be understood by reference to the drawings. The reader will note that the same reference numerals appear in multiple figures. Where this is the case, the numerals refer to the same or corresponding structure in those figures.

As shown in FIG. 1, delivery system 10 includes fluid reservoir 12, fluid pump 14, gas source 16, high pressure gas exchanger 18, delivery tube 36, and one or more arrays of capillary channels 20. High pressure gas exchanger 18 preferably includes an outer gas tight housing surrounding semi-permeable membrane gas-fluid interface 26, such as an oxygenator, which comprises a gas permeable and at least substantially fluid impervious container. Differential pressure gauge 22 is provided to measure the difference between the gas pressure in interior 40 and the hydrostatic pressure within gas-fluid interface 26. Differential pressure gauge 22 and other suitable controls are provided to maintain a near constant hydrostatic pressure within gas-fluid interface 26 approximately 1% to 20%, higher than the gas pressure in interior 40 within housing 34 of high pressure gas exchanger 18. The higher hydrostatic pressure within gas-fluid interface 26 facilitates the dissolution of gas in the fluid in interior 40.

Delivery system 10 may also include a fluid filter 24 to filter fluid before it enters fluid reservoir 12. Fluid filter 24 is preferably a standard, commercially available filter such as porous sintered metal filters manufactured by Mott Metallurgical.

Fluid pump 14 pumps fluid from fluid reservoir 12 into gas-fluid interface 26 via input tube 28. As previously described, gas-fluid interface 26 is located within gas exchanger 18 surrounded by gas containing interior space 40. Gas-fluid interface 26 preferably incorporates silicone, such as silicone membranes or silicone tubules, as the gas exchanging media. Hollow microporous polypropylene tubes may also be used as a gas exchanging media. Where gas source 16 contains a corrosive gas such as ozone, gas-fluid interface 26 is made of corrosive resistant materials such as certain plastics, stainless steel, glass, Kevlar, silicone, silicone rubber or platinum, and gold plated soft metal seals may also be utilized.

Output 30 of gas-fluid interface 26 is coupled to output 32 of high pressure gas exchanger 18, which is in turn coupled to output tube 36. Fluid exits output tube 36 via capillary channels 20.

Capillary channels 20 are preferably cylindrical, and have a relatively small diameter which helps to stabilize the gas supersaturated fluid upon ejection. Capillary channels 20 may also have slit-like, rectangular, square, triangular, and annular cross-sectional shapes.

Where channels 20 have a circular cross-section, the inner diameter of each of capillary channels 20 is preferably within the approximate range of 25 to 300 $\mu$m. Using capillary channels with inner diameters of less than about 25 $\mu$m is possible, but may require a large number of such channels to be used to compensate for the higher flow resistance. In addition, the use of capillary channels with inner diameters of less than about 25 $\mu$m may also increase the likelihood that such channels will become blocked with particulates. On the other hand, the use of capillary channels with inner diameters larger than about 300 $\mu$m may not effectively stabilize fluids supersaturated gases, such as oxygen, at high partial pressures.

Capillary channels 20 are preferably non-hydrophobic with a smooth inner surface. Although plastic channels (such as polyimide channels), and metal channels (such as stainless steel channels), can be used, glass or silica channels generally provide a smoother inner surface, are less expensive to obtain commercially, and large arrays of parallel glass or silica channels can be easily fabricated. Moreover, large numbers of parallel channels within glass plates may also be easily obtained commercially. Glass and silica provide the additional benefit of being chemically inert in many environments, and thus are less likely to react with the gas-supersaturated fluid. Glass and silica channels can also be cleaned with harsh solvents with little or no damage.

In operation, gas is delivered from gas source 16 to interior 40 of high pressure gas exchanger 18 via gas input tube 38. Preferably, gas within interior 40 of high pressure gas exchanger 18 is maintained at a pressure of approximately 8 to 50 bar. Differential pressure gauge 22 and other suitable controls are provided to maintain a near constant hydrostatic pressure within gas-fluid interface 26 approximately 1% to 20% higher than gas pressure within interior 40 of high pressure gas exchanger 18. More preferably, the near constant hydrostatic pressure within gas-fluid interface 26 is approximately 9 to 51 bar, which is slightly higher than the gas pressure within interior 40 of high pressure gas exchanger 18.

One example of a suitable control is to adjust the rate of the fluid flow from fluid pump 14 into gas-fluid interface 26. Pressure differential gauge 22 may provide electrical signals to fluid pump 14 and/or to gas source 16 via electrical signals carrier 48. Thus, in response to the electrical signals, fluid flow rate from fluid pump 14 would be adjusted accordingly so as to achieve and maintain proper hydrostatic pressures within gas-fluid interface 26 and proper pressure differences between the hydrostatic pressure and the gas pressure within interior 40. Another example of a suitable control is to adjust the rate of the fluid flow from gas exchanger 18 to the site of interest by adjusting fluid valve 23 so as to achieve and maintain proper hydrostatic pressures within gas-fluid interface 26 and proper pressure differences between the hydrostatic pressure and the gas pressure within interior 40. Where a variable fluid flow rate from gas exchanger 18 to the site of interest is desired, differential pressure gauge 22 regulates the gas flow rate from gas source 16 and regulates a gas release valve (not shown) for selective release of gas from within gas exchanger 18 in order to vary the fluid flow rate from gas exchanger 18.

Because the peak hydrostatic pressure required for the fluid in delivery system 10 (i.e. fluid in input tube 28, gas-fluid interface 26, and delivery tube 36) is approximately 1% to 20% higher than the gas partial pressure, overt gas pockets in the gas-supersaturated fluid do not create active, bubble generating gas nuclei at the tube-liquid interface. Because the pressure differential prevents generation of active, bubble generating gas nuclei, the need for a dwell time for dissolving gas nuclei in the fluid and the corresponding need for a high pressure vessel to provide the dwell time are eliminated. Once fluid valve 23 is opened and a constant supply of fluid from fluid reservoir 12 is established, stabilized flow of gas-supersaturated liquid into a gas-depleted site of interest via output tube 36 and capillary channels 20 can proceed continuously with minimum supervision.

Figure 2:
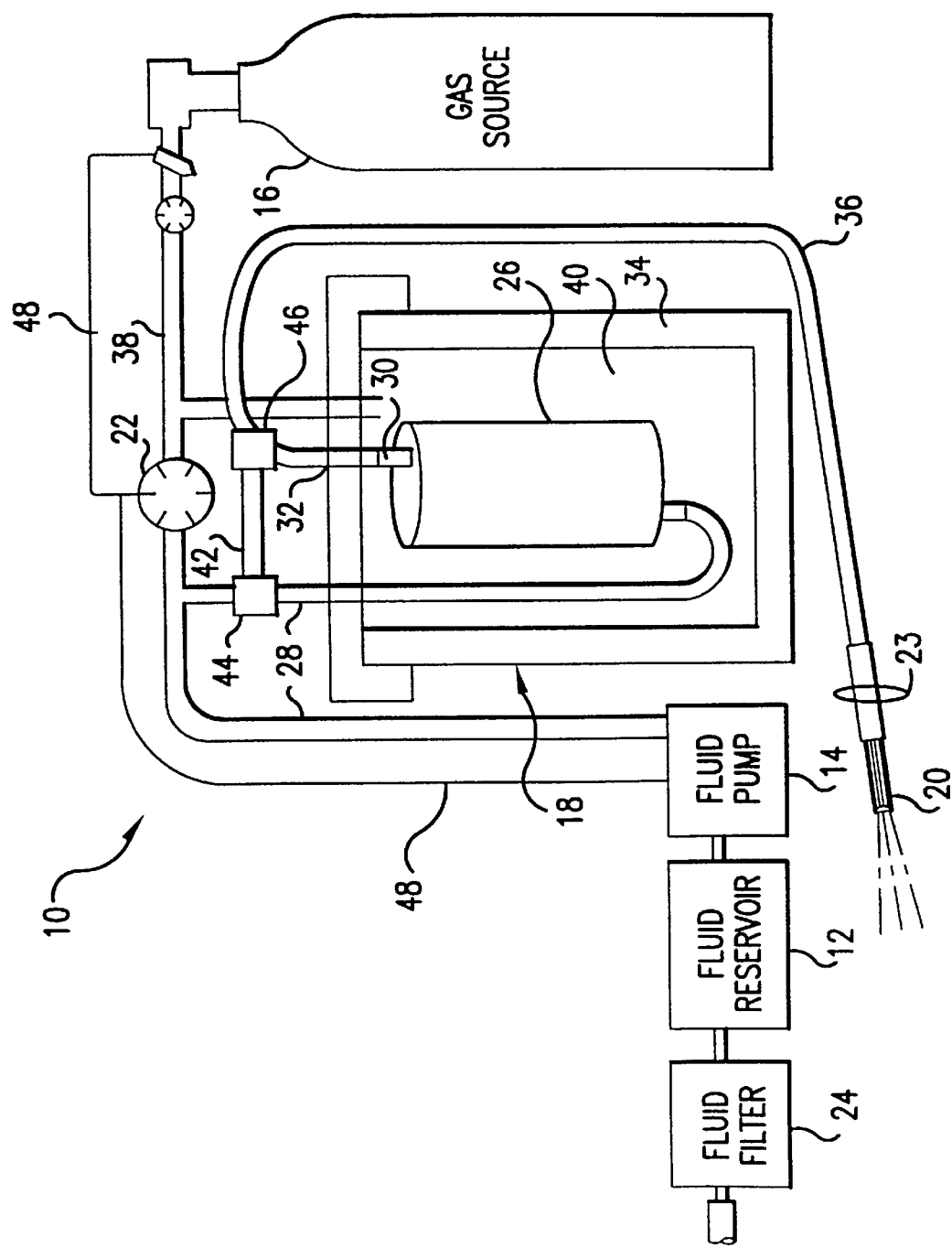
FIG. 2 shows a system for delivery of gas-supersaturated fluids according to an alternative embodiment.

Referring now to FIG. 2, delivery system 10 may be configured such that gas-deficient fluid pumped by fluid pump 14 can bypass high pressure gas exchanger 18 via bypass tube 42 and be delivered to capillary channels 20 via output tube 36, for initial flushing of capillary channels 20.

Delivery system 10 may further provide valves 44, 46 which may be in an initial bypass position or an operational position. During the initial flushing, valves 44, 46 are in the initial bypass position which allow fluid to flow from input tube 28 directly to output tube 36 via bypass tube 42 and prevent fluid from entering high pressure gas exchanger 18. After the initial flushing procedure, valves 44, 46 are in the operational position which allow fluid to flow from input tube 28 to output tube 36 via high pressure gas exchanger 18 and prevent fluid from entering bypass tube 42.

This procedure of flushing capillary channels 20 facilitates elimination of surface nuclei within capillary channels 20 because the surface gas nuclei can be relatively easily absorbed by the gas-deficient fluid and because the velocity of the fluid flow through channels 20 may result in flushing out the surface gas nuclei from channels 20. Thus, the initial flushing procedure may be used to facilitate high volume delivery of gas-supersaturated fluid to the site of interest without cavitation inception despite a relatively low hydrostatic pressure of approximately 9 to 51 bar.

Delivery of gas-supersaturated fluid through capillary channels 20 at a high velocity provides an additional mechanism for reducing or eliminating gas nuclei at the interface between the inner surface of capillary channels 20 and the gas-supersaturated fluid. Specifically, high velocity flow may reduce or eliminate gas nuclei at the channel-fluid interface due to a possible Venturi effect at the channel-fluid interface. The high velocity flow and possible associated Venturi effect acts to flush gas nuclei from the inner surface of capillary channels 20 before the gas nuclei can grow large enough to become active and cause trains of bubbles to form.

High velocity flow further inhibits bubble formation because there is insufficient time for nucleation and bubble growth in the fluid within capillary channels 20, before the fluid exits the capillary channels. After the gas-supersaturated fluid exits capillary channels 20, subcritical bubble nuclei, i.e. a bubble nuclei of size insufficient for bubble formation, are reabsorbed into the fluid and relatively rapid mixing of the fluid with liquids in the external environment occurs under ambient atmospheric pressure.

The velocity of fluid exiting capillary channels 20 is preferably greater than 0.05 m/sec, and more preferably in the range of 0.5 m/sec to 10 m/sec. As an example, a parallel array of 55 fused silica capillary channels 20 each having an inner diameter of about 150 $\mu$m and a length of about 10 cm can be used to deliver 800 ml/min of water containing oxygen dissolved at a partial pressure of 20.5 bar, at a hydrostatic pressure of 22.5 bar. The mean flow velocity of the oxygen-supersaturated water through each channel 20 would be approximately 13 m/sec.

Applications for preferred embodiments include many different gas-liquid combinations, which may be a mixture of a plurality of gases and/or liquids.

For example, system 10 may be used for relatively quick and inexpensive large scale delivery of oxygen-supersaturated water into fluid requiring aeration, such as potable water, municipal water, wastewater, water in bioreactors, fisheries, ponds, lakes, streams, wells, swimming pools, baths and hot tubs. oxygenation of such bodies of water using oxygen supersaturated liquid generated by system 10 would be more rapid than aeration by directly pumping gas into the site of interest, and allows precise control of the final oxygen concentration in the site of interest.

In addition, relatively high oxygen concentrations, for example, 10 mg/L or greater, can be achieved in the external environment because the preferred embodiments provide a gas transfer efficiency of nearly 100%; thus, almost all of the dissolved gas delivered is absorbed by the oxygen-deficient body of water. As a result, a relatively smaller volume of oxygen-supersaturated water is required to adequately aerate an oxygen-deficient body of water. For example, the volume of water super-saturated with oxygen at 21 bar partial pressure necessary to adequately aerate wastewater would be a small fraction of the volume of the wastewater, depending on the B.O.D. (biologic oxygen demand) level. Furthermore, for treatment of many types of large bodies of gas-deficient fluids, a small portion of the fluid, after filtration, can be used as the fluid source for preparation of the gas-supersaturated fluid to be recycled back into the large body of fluid. Thus, by utilizing gas-deficient fluid from the body of fluid to be aerated as a fluid source, the volume of body of fluid is not increased.

Hyperbaric gas concentration levels are achievable in the external body of fluid to be aerated. If the mean velocity of the effluent is relatively low, for example less than 5 m/sec, and the volume of fluid in the external body of fluid is small relative to the effluent volume flow rate per minute, for example ratios of 10:1, resulting in a turnover of gas-supersaturated water approximately every 10 minutes, a hyperbaric gas level can be achieved and maintained in the external body of fluid.

When such an approach is utilized to deliver an oxygen-supersaturated effluent to an external body of fluid, an oxygen bath is thereby provided where the $PO_2$ in the external body of fluid is in the range of at least approximately 5–10 bar. Such an oxygen bath may be utilized for neonates and infants with respiratory insufficiency to increase the oxygen levels in the general circulation. Both the higher permeability of human neonatal skin relative to that of adults and the relatively high ratio of the neonatal body surface area to the neonatal body volume facilitate the transport of oxygen from the oxygen bath across the skin into the general circulation. For older individuals, the high oxygen level in an oxygen bath may also be utilized to enhance healing of superficial wounds, such as burns, and to enhance collagen synthesis of otherwise normal, but relatively oxygen-poor skin.

Another application of preferred embodiments is the infusion of ozone-supersaturated fluid into various types of fluids. The ozone may be generated, for example, within gas source 16 or within housing 34 of high pressure gas exchanger 18 by utilizing high voltage arcs. Ozone-supersaturated fluid infusion can be used for disinfection, flocculation, oxidation of dissolved metals, odor control, and oxidation of organic material.

For example, when system 10 is used for the delivery of an effluent supersaturated with a non-toxic gas into, for example, wastewater, microorganisms and other organic matters may grow and accumulate on gas-fluid interface 26 over time, thereby reducing its gas transfer efficiency. To alleviate or eliminate such growth and accumulation, system 10 may also be used for the periodic and temporary delivery of ozone-enriched or ozone-supersaturated fluid. The ozone would kill the microorganisms and oxidize the organic materials, which would then be more easily flushed from gas-fluid interface 26. In addition or alternatively, a suitable solvent such as alcohol, acetone, or a strong acid or base may be flushed through gas exchanger 18 to clean gas-fluid interface 26 of microorganisms and organic matter. Thus, the periodic and temporary delivery of effluent containing ozone and/or a suitable solvent would sterilize and disinfect system 10 of organic elements as well as to flush out any accumulated debris. Furthermore, because of the relatively high solubility of ozone in water, a high ozone concentration can be achieved at partial pressures of only approximately 3 to 10 bar.

A concern with infusing ozone-supersaturated fluid into a site of interest is that the half-life of ozone in ordinary tapwater is generally in the range of 10 to 20 minutes. Thus, because of the half-life of ozone, rapid delivery of ozone-supersaturated fluid is desirable. By using system 10, ozone-supersaturated water from high pressure gas exchanger 18 can be delivered at high velocities via capillary channels 20 within a few seconds, resulting in very little loss of activity of the dissolved ozone. And because the ozone delivered remains dissolved (that is, it does not bubble out of fluid) there is less concern that ozone will enter the atmosphere. As a result, the ozone-supersaturated water can be used to treat open bodies of water, such as reservoirs, lakes, ponds, streams, rivers, swimming pools, as well as groundwater, well water, and water within closed chambers.

Bioreactors often use carbon monoxide as a carbon source for synthesis of organic compounds by anaerobic bacteria. Because carbon monoxide has a low solubility in water and consumption of the gas by the anaerobic bacteria can be relatively high, it may be difficult to maintain a sufficient carbon monoxide supply in a bioreactor. An infusion of carbon monoxide-supersaturated water generated by system 10 could be used to provide an efficient and controlled means for increasing the level of carbon monoxide in a bioreactor. Other gases, such as nitrogen sources, may be useful for the growth of other types of organisms.

To extinguish a fire, it may be desirable to deliver a fluid supersaturated with an inert gas, such as nitrogen or carbon dioxide, rapidly to the fire without premature liberation of the inert gas from its dissolved state in the fluid. Upon high velocity delivery of fluid supersaturated with an inert gas, a fire can be extinguished with greater efficiency than with the use of water alone because of the displacement of oxygen in the air with the inert gas, cooling of the fluid during gas expansion, and the dispersion of the fluid upon gas expansion.

Liquids other than water may also be used in system 10 to deliver a high concentration of a gas or a mixture gases to a site of interest. For example, many liquid fuels, such as diesel fuel, gasoline, kerosene and alcohols, may burn more efficiently with a high oxygen concentration. System 10 may be utilized to eject the fluid into a combustion chamber, such as the cylinders of an engine. The high solubility of oxygen in most fuels, such as gasoline and diesel fuel, results in a high oxygen concentration at relatively low partial pressures. In addition to greater combustion efficiency provided by a high concentration of oxygen, the improved oxidation of the fuel could reduce some toxic gaseous byproducts associated with incomplete combustion.

Another application of the system of the present invention is snow making by ejecting water supersaturated with air into air having an ambient temperature slightly higher than 0° C. When the air-supersaturated water exits capillary channels 20 into the atmospheric environment, there is a drop in hydrostatic pressure of the water which results in a rapid expansion of the gas. Because the rapid expansion of the gas lowers the temperature of the fluid, freezing of water droplets can occur despite an air temperature higher than 0° C.

In contrast, typical prior art snowmaking equipment uses large fans to propel water from a hose into air that is at or below 0° C. With the prior art equipment, small water droplets and ice crystals form and are propelled into the air by the force of the fans. However, because an intact stream of water can relatively easily be propelled further than water droplets and ice crystals can be propelled with the force of the fans, the prior art snowmaking equipment does not achieve as great a maximum distance as the system of the present invention. With the system of the present invention, the air-supersaturated water fluid can remain as an intact stream for sufficiently long periods because of the high flow velocity of the fluid. Due to gas bubbles nucleating from the fluid and normal hydrodynamic forces, such as Rayleigh instability, the fluid fragments in the air and form water droplets, fragments, and/or bubbles. The associated drop in temperature from expansion of the dissolved gas then freezes the water to produce artificial snow.

The present invention has been described in terms of preferred embodiments. The invention, however, is not limited to the embodiment depicted and described. Rather, the scope of the invention is defined by the appended claims.

What is claimed is:

1. A method for providing gas-supersaturated fluid to an environment, comprising the steps of:
   delivering fluid under pressure from a fluid source to a gas exchanger;
   delivering gas under pressure from a gas source to the gas exchanger;
   controlling the pressures of the fluid and gas such that the pressure of the fluid within the gas exchanger is greater than the pressure of the gas within the gas exchanger; and
   delivering the gas-supersaturated fluid from the gas exchanger to the environment through one or more channels in fluid communication with the gas exchanger without cavitation inception.

2. The method according to claim 1, wherein the one or more channels have inner diameters of between about 25 $\mu$m and about 300 $\mu$m.

3. The method according to claim 1, wherein the one or more channels have inner diameters of about 100 $\mu$m.

4. The method according to claim 1, wherein the gas comprises one of ozone and oxygen.

5. The method according to claim 1, wherein the pressure of the fluid within the gas exchanger is between about 1% and about 20% greater than the pressure of the gas within the gas exchanger.

6. The method according to claim 1, wherein gas-enriched fluid is delivered to the environment at a fluid flow velocity of greater than about 0.05 m/sec.

7. The method according to claim 1, wherein the environment comprises a supply of wastewater.

8. The method according to claim 1, wherein the environment comprises a bioreactor.

9. The method according to claim 1, further comprising the step of:
   filtering the fluid prior to delivery of the fluid to the gas exchanger.

10. The method according to claim 1, wherein the controlling step comprises the step of:
    adjusting the fluid flow to the gas exchanger in response to a signal from a pressure differential gauge assembly in fluid and in gaseous communication with the gas exchanger.

11. The method according to claim 1, wherein the controlling step comprises the step of:
    adjusting the gas flow to the gas exchanger in response to a signal from a pressure differential gauge assembly in fluid and in gaseous communication with the gas exchanger.

12. The method according to claim 1, wherein the gas-enriched fluid flow to the environment is adjusted in response to a signal from a pressure differential gauge assembly in fluid and in gaseous communication with the gas exchanger.

13. The method according to claim 1, wherein the gas-enriched fluid delivered to the environment comprises a gas-supersaturated fluid.

14. The method according to claim 1, wherein the gas source comprises a supply of gas provided from a gas generator.

15. The method according to claim 14, wherein the gas generator comprises an ozone generator.

16. The method according to claim 1, wherein the gas exchanger comprises a housing enclosing a gas-fluid interface and gas.

17. The method according to claim 16, wherein the gas-fluid interface is at least partially made of silicone.

18. The system according to claim 16, wherein the gas-fluid interface is made of corrosion resistant materials.

19. The method according to claim 1, wherein the fluid pressure in the gas exchanger is controlled by adjusting one or more valves in fluid communication with the one or more channels.

20. The method according to claim 1, wherein one or more of the channels is made of silica.

21. The method according to claim 1, wherein one or more of the channels is made of glass.

22. The method according to claim 1, wherein one or more of the channels is made of metal.

23. The method according to claim 1, wherein one or more of the channels is made of a ceramic.

24. The method according to claim 1, wherein the fluid source is in fluid communication with the one or more channels such that fluid may bypass the gas exchanger and flow from the fluid source to the one or more channels.

25. A method for providing gas-enriched fluid to a delivery site, comprising:

providing a gas-enriched fluid generator comprising a gas port, a fluid inlet port, and a fluid outlet port; and providing a fluid transport for transporting fluid from the gas-enriched fluid generator to the delivery site, the fluid transport comprising a first end and a second end, wherein the first end is connected to the fluid outlet port and the second end is disposed proximate the delivery site, wherein the fluid transport comprises a plurality of channels proximate the second end, and wherein the channels are sized to deliver the gas-enriched fluid in a bubble-free manner.

26. The method according to claim 25, wherein the gas port of the gas-enriched fluid generator is in gaseous communication with a pressurized gas source.

27. The system according to claim 26, wherein said source of gas comprises a gas generator.

28. The method according to claim 25, wherein the fluid inlet port of the gas-enriched fluid generator is in fluid communication with a pressurized fluid source.

29. The method according to claim 28, wherein the fluid transport is in fluid communication with the fluid source such that fluid may bypass the gas-enriched fluid generator and flow from the fluid source to the fluid transport.

30. A The method according to claim 25, further comprising the step of:

controlling pressures within the gas-enriched fluid generator such that the pressure of the fluid is greater than the gas pressure.

31. The method according to claim 30, wherein the pressure of the fluid is between about 1% and about 20% greater than the gas pressure.

32. A method for delivering gas-supersaturated fluid comprising:

providing means for receiving a fluid and a gas;

providing means for controlling pressures of the gas and of the fluid to create the gas-supersaturated fluid; and providing means for delivering the gas-supersaturated fluid in a bubble-free manner.

33. The method according to claim 25, wherein the gas-enriched fluid delivered is a gas-supersaturated fluid.

34. The method according to claim 32, wherein the gas-supersaturated fluid comprises oxygen-supersaturated fluid.

35. The method according to claim 32, wherein the gas-supersaturated fluid comprises ozone-supersaturated fluid.

36. The method according to claim 25, wherein the plurality of channels comprise capillaries.

37. The method according to claim 25, wherein the gas-enriched fluid comprises oxygen-enriched fluid.

38. The method according to claim 25, wherein the gas-enriched fluid comprises ozone-enriched fluid.

* * * * *